(12) United States Patent
Ahari et al.

(10) Patent No.: US 9,636,189 B2
(45) Date of Patent: May 2, 2017

(54) METHOD FOR ENHANCING ULTRASOUND VISIBILITY OF HYPERECHOIC MATERIALS

(71) Applicant: Devicor Medical Products, Inc., Sharonville, OH (US)

(72) Inventors: Frederick A. Ahari, Belleair Beach, FL (US); John S. Fisher, Belleair, FL (US)

(73) Assignee: DEVICOR MEDICAL PRODUCTS, INC., Sharonville, OH (US)

( * ) Notice: Subject to any disclaimer, the term of this patent is extended or adjusted under 35 U.S.C. 154(b) by 882 days.

(21) Appl. No.: 13/911,708

(22) Filed: Jun. 6, 2013

(65) Prior Publication Data

US 2013/0274893 A1    Oct. 17, 2013

Related U.S. Application Data

(62) Division of application No. 11/277,721, filed on Mar. 28, 2006, now Pat. No. 8,939,910.

(51) Int. Cl.
*A61K 8/00* (2006.01)
*A61B 90/00* (2016.01)
(Continued)

(52) U.S. Cl.
CPC ............... *A61B 90/39* (2016.02); *A61F 2/02* (2013.01); *A61K 49/226* (2013.01); *A61L 31/06* (2013.01);
(Continued)

(58) Field of Classification Search
CPC ...................................... A61B 90/39
See application file for complete search history.

(56) References Cited

U.S. PATENT DOCUMENTS 4,774,957 A   10/1988 Nambu et al.
5,423,736 A    6/1995 Cartmell et al.
(Continued)

FOREIGN PATENT DOCUMENTS

EP      1579878        9/2005
WO      0038579 A2    7/2000
(Continued)

OTHER PUBLICATIONS

International Search Report for PCT/US2008/086376 (filing date of Dec. 11, 2008) with a mailing date of Jul. 23, 2009 Applicant: Biopsy Science, LLC et al.
(Continued)

*Primary Examiner* — Paul Dickinson
(74) *Attorney, Agent, or Firm* — Arent Fox LLP

(57) ABSTRACT

A hydrogel plug is placed under stress during its curing stage, in one embodiment, by application of an externally applied force. The stress may also be induced during or after the dehydration process. The direction of the externally applied force increases the length, width, depth, or radial extent of the plug. The elastic limit of the plug is exceeded when the external force is applied so that the plug substantially retains its stressed size and shape when the externally applied force is removed. When the stretched or otherwise deformed dehydrated plug is hydrated, it substantially returns to the configuration it had prior to its dehydration and prior to the application of the externally applied force.

8 Claims, 2 Drawing Sheets

(51) Int. Cl.
*A61F 2/02* (2006.01)
*A61K 49/22* (2006.01)
*A61L 31/06* (2006.01)
*A61L 31/14* (2006.01)

(52) U.S. Cl.
CPC ..... *A61L 31/145* (2013.01); *A61B 2090/3908* (2016.02); *A61B 2090/3925* (2016.02); *A61B 2090/3995* (2016.02)

(56) References Cited

U.S. PATENT DOCUMENTS

| | | | |
|---|---|---|---|
| 5,489,437 | A | 2/1996 | Marra |
| 5,578,661 | A | 11/1996 | Fox et al. |
| 5,873,827 | A | 2/1999 | Russell |
| 5,882,557 | A | 3/1999 | Hayakawa et al. |
| 6,106,473 | A | 8/2000 | Violante et al. |
| 6,312,457 | B1 | 11/2001 | DiMatteo et al. |
| 6,372,248 | B1 | 4/2002 | Qin et al. |
| 6,544,185 | B2 | 4/2003 | Montegrande |
| 6,723,781 | B1 | 4/2004 | Frate et al. |
| 6,725,083 | B1 | 4/2004 | Burbank et al. |
| 7,329,414 | B2 | 2/2008 | Fisher et al. |
| 7,556,602 | B2 | 7/2009 | Wang et al. |
| 8,280,486 | B2 | 10/2012 | Miller et al. |
| 2003/0109899 | A1 | 6/2003 | Fisher et al. |
| 2003/0165569 | A1 | 9/2003 | Levy et al. |
| 2004/0030262 | A1 | 2/2004 | Fisher et al. |
| 2004/0042582 | A1 | 3/2004 | Ein-Gal |
| 2005/0148995 | A1 | 7/2005 | Shepard et al. |
| 2005/0234336 | A1 | 10/2005 | Beckman et al. |
| 2005/0240098 | A1 | 10/2005 | Zhong et al. |
| 2006/0100664 | A1 | 5/2006 | Pai et al. |
| 2006/0193892 | A1 | 8/2006 | Furst et al. |
| 2006/0293581 | A1 | 12/2006 | Plewes et al. |
| 2007/0239016 | A1 | 10/2007 | Fisher |
| 2008/0208347 | A1* | 8/2008 | Muratoglu ............ A61L 27/52 623/18.11 |

FOREIGN PATENT DOCUMENTS

| | | |
|---|---|---|
| WO | WO 00/45854 A2 | 8/2000 |
| WO | 0162135 A2 | 8/2001 |

OTHER PUBLICATIONS

Preliminary Report of Patentability for PCT/US08/86376 (filing date of Dec. 11, 2008) with a mailing date of Mar. 30, 2011, Applicant: Biopsy Sciences, LLC.

International Search Report for PCT/US07/04354 (filing date of Feb. 20, 2007) with a mailing date of Jan. 28, 2008, Applicant: Biopsy Science, LLC.

Preliminary Report of Patentability for PCT/US2007/004354 (filing date of Feb. 20, 2007) with a mailing date of Oct. 9, 2008, Applicant: Biopsy Sciences, LLC et al.

European Office Action mailed May 22, 2015 for corresponding European Application No. 08 872 137.8.

Benedetto et al., "Patterning Polyacrylamide hydrogels by soft lithography", Nanotechnology, vol. 16, 2005, pp. 165-170.

* cited by examiner

METHOD FOR ENHANCING ULTRASOUND VISIBILITY OF HYPERECHOIC MATERIALS

CROSS-REFERENCE TO RELATED APPLICATION

This application claims the priority of U.S. patent application Ser. No. 11/277,721, filed Mar. 28, 2006 (now U.S. Pat. No. 8,939,910). The disclosure of the priority application is incorporated in its entirey herein by reference.

BACKGROUND OF THE INVENTION

1. Field of the Invention

This invention relates, generally, to a method for improving the visibility of a hyperechoic marker under ultrasound. Such markers are used to indicate the location of a tumor or lesion so that a procedure to remove such lesion or tumor may be performed weeks or months after the marker has been implanted. More particularly, it relates to markers that incorporate hydrogels to enhance the visibility of the markers with imaging techniques such as ultrasound and to methods for making such markers.

2. Description of the Prior Art

A permanent metal or hard plastic, such as a permanent, bio-compatible plastic such as polyethylene, or bioabsorbable, biocompatible plastic such as PGA/PLA, or other suitable marker must be left at a biopsy site at the completion of a biopsy if the site is to be located again in the future. Biodegradable markers are not permanent and therefore cannot be relied upon if a biopsy site is to be re-located at a time remote from the time of the biopsy. Suture and collagen-based markers are not suitable as markers because they are hyperechoic, i.e., difficult to see under ultrasound because such materials are easily confused with other shadowing normal structures in the body such as fibrous tissue, fatty tissue, ducts in breast tissue, and the like, for example. Such tissue provides a background clutter that masks the presence of a marker made of metal, hard plastic, or other hyperechoic material.

Water, unlike metal, hard plastic, and other hyperechoic materials, is hypoechoic, i.e., easy to see under imaging techniques such as ultrasound. Therefore it would be advantageous if a marker made of a hyperechoic material such as metal or hard plastic could be surrounded by an easily seen quantity of water.

However, the art includes no means for surrounding a hyperechoic marker with water at a biopsy site. There is a need, then, for a permanent marker that is surrounded by water after it has been positioned at a biopsy site.

A need also exists for a hydrogel manufacturing process that produces a cured and dehydrated plug or marker that contracts in length and increases in diameter upon being hydrated.

There is also a need for a hydrogel manufacturing process that produces a cured and dehydrated plug or marker that contracts in width and increases in length and height upon being hydrated.

There is also a further need for a hydrogel manufacturing process that produces a cured and dehydrated plug or marker that contracts radially and increases in length upon being hydrated.

However, in view of the prior art taken as a whole at the time the present invention was made, it was not obvious to those of ordinary skill how the identified needs could be fulfilled.

SUMMARY OF THE INVENTION

The long-standing but heretofore unfulfilled need for a dehydrated marker that encapsulates a permanent marker and that facilitates imaging of said permanent marker is met by this new, useful, and non-obvious invention.

The long-standing but heretofore unfulfilled need for a dehydrated marker that contracts in length and increases in diameter, contracts in width and increases in length, or radially contracts and increases in length when hydrated, and a method for making such a markers, is also met by this invention.

Hydrogel, in order to be effective in the application of this invention, should contain about eighty to ninety percent (80%-90%) water. Hydrogels can contain higher or lower percentages of water but the range of eighty to ninety percent is believed to be optimal for the purposes of this invention but this invention is not limited to that particular range. Forming a biopsy marker from a hydrogel therefore provides a way to contain water so that it does not flow. It would be advantageous to embed a permanent marker within a cured and dehydrated hydrogel marker or plug. The plug would become hydrated by natural body moisture after being positioned at a biopsy site, thereby surrounding the permanent marker with water. The water would be easily seen under ultrasound and therefore the marker it surrounds would be easy to see.

The permanent marker may be positioned in the center of the hydrogel or off-center with respect thereto. It may even be positioned external to the hydrogel. In the latter case, a record may be made to the effect that the marker will be found at the six o'clock position relative to the hydrogel, or the like.

Current hydrogel manufacturing processes provide a cured and dehydrated product that expands in all directions when hydrated. Such all-dimensional expansion may be unwanted in some situations. For example, a cavity may have a certain diameter and length. In that situation, it may be desirable to insert a plug having slightly less diameter and about the same length as the cavity. The desired plug would expand in diameter, thereby sealing the cavity, but not increase in length when hydrated. As another example, a cavity may have a certain width, height, and length and it may be desirable to insert a plug having a slightly smaller width and height and about the same length as the cavity. It would then be desirable to have a plug that expands in width and height to seal the cavity but not longitudinally when exposed to the natural moisture of the body.

The novel hydrogel polymer has a permanent marker formed of metal, hard plastic, or other hyperechoic material embedded within the polymer. The hydration of the polymer by the natural moisture of the tissue surrounding it causes expansion of the polymer and thus minimizes the risk of migration. The growing hydrogel centers itself in the biopsy cavity as it grows.

The novel hydrogel composition does not include PGA/PLA. It is preferably peg-based and has advantages in imaging. Specifically, the plug is mostly water when hydrated. This provides a significant advantage because water is easily visible when ultrasound is employed as aforesaid.

The novel marker has two (2) imaging stages. The plug is solid and dry when it is deployed initially to mark the cavity created by a biopsy procedure. The solid, dry plug is seen as a shadowing, hyperechoic, linear object with posterior acoustic shadowing on ultrasound.

However, as the hydrogel expands, naturally-present moisture from the surrounding tissue, the hydration enables increasing sound through transmission, appears more and more hypoechioc and is easy to visualize on follow up ultrasound studies. The hydrogel, when hydrated, appears black in color, centers itself in the biopsy or other cavity as it grows, and frames the permanent marker.

The polymer plug is molded and cured into different shapes to avoid confusion with normal breast structures such as ducts. The shapes can be rod-like, spiral, round, toroidal, rectangular, string of pearls or any other predetermined geometrical configuration that does not have an appearance that resembles a naturally-occurring feature.

The hypoechoic nature of the hydrated plug enables ultrasound visibility of the permanent marker within the hydrogel hydrated plug because the permanent marker is outlined as a specular reflector within a hypoechoic hydrated marker plug having a water-like nonreflective substrate.

Water is the most easily visualized substrate under ultrasound. The permanent marker of this invention can have any shape that is not easily confused with a natural shape as mentioned above and it can be made of any permanent metallic-like or hard plastic material. Helical shapes having a hollow interior is a preferred shape because it allows the polymer to better retain the marker within.

This invention incorporates two novel ideas that lead to patentable applications. Both ideas involve different manufacturing techniques to produce a unique design that provides unique and novel properties for different medical, i.e., implantable applications.

The first insight relates to stress induction. Hydrogels have some unique properties due to their hydrophilic characteristics. One of the most important properties of this type of implantable polymer is the ability to expand to fill a void or cavity to thereby mark a specific site in many different types of tissue. Significantly, the hydrogel implants of this invention are manufactured so that they can expand or contract in one dimension only when desired, two dimensions only when desired, or all three dimensions when desired.

These novel manufacturing processes are introduced during different stages of manufacturing to control post hydration expansion.

In the first novel method, stress is induced in the hydrogel during the curing process. Significantly, the hydrogel is pulled beyond its elastic limit. Specifically, stress is induced during the curing process by stretching the hydrogel beyond its elastic limit in the length direction. This increase in length decreases the diameter of the hydrogel plug if it is in rod form. This introduction of stress while the hydrogel is changing from a liquid to a solid stage creates a solid, dry marker that contracts in length and expands in diameter only when hydrated. Stress may also be induced during the curing process by stretching the hydrogel beyond its elastic limit in the width direction, thereby shortening its length. This causes the hydrogel to contract in the width direction and expand in the length direction when hydrated. Stress may further be induced during the curing process by stretching the hydrogel beyond its elastic limit in the height direction. This causes the hydrogel to contract in the height direction and expand in length when hydrated. Moreover, stress may be induced during the curing process by stretching the hydrogel beyond its elastic limit in the radial direction. This causes the hydrogel to contract only in the radial direction when hydrated. To accomplish radial stretching, the hydrogel is formed into a cylinder and pressure is applied from within to cause the radial expansion. Such radial expansion shortens the length of the cylinder. Thus, when hydrated, the hydrogel contracts in a radial direction and lengthens.

In a second novel method, stress is induced during the dehydration process. The product is pulled or suspended beyond its elastic limit in a specific direction to increase its length, width, depth, or radial dimension. This causes the polymer to contract in that specific direction to the substantial exclusion of all other directions when the polymer is hydrated.

This process can be used to make the polymer expand radially and contract in a longitudinal direction as aforesaid. The stress induced during this process is controlled to determine the Radial Expansion/Longitudinal Contraction ratio (RE/LC). Profile expansion or radial expansion is desirable when a cavity or a biopsy tract needs to be sealed in the substantial absence of longitudinal expansion. This technique enables the marker manufacturer to produce markers having known RE/LC ratios.

In a third novel method, stress is induced after dehydration of the polymer has been completed. The stress may also be induced by stretching or by introducing different mechanical deformations by means other than stretching. Some of these deformations are achieved by using mechanical processing equipment having various functions such as punching, folding, and the like. In all cases, the deformation must exceed the elastic limit of the material.

The permanent metallic or hard plastic marker may have a rod shape, a cylindrical shape, a coil shape, or other suitable shape. The coil configuration allows hydrogel to cure inside the core of the coil and between the loops of the coil to achieve a complete and smooth coverage of the hyperechoic marker by the hypoechoic hydrogel.

The novel marker has several medical applications for soft tissue implants with a controlled RE/LC ratio. For example, it may be used as a soft tissue or void filler in cosmetic applications. A physician would start with a small size implant that expands in time to fill a cavity in a radial direction only without any longitudinal expansion.

Hydrogel implants post hydration are softer than most conventional implants and can take different shapes in filling soft tissue cavities. Expansion in the length direction may need to be controlled to maintain the desired shape.

There are also applications that require a higher than usual expansion rate, and there are applications where higher expansion rates are needed for small dehydrated implants in one direction only while contraction or shrinkage occurs in a different direction.

A primary advantage of the novel markers is that they provide a metal, hard plastic, or other permanent marker that is easy to see under imaging because it is surrounded by water due to the hydration of the hydrogel within which it is embedded.

Another major advantage is the ability to cause a hydrogel plug to expand or contract in a predetermined manner when hydrated. In all embodiments, the hydrated plug returns to or substantially to the size and shape it had prior to the application thereto of an externally applied force and prior to its dehydration. This is the "in repose" configuration of the hydrogel plug. The externally applied force may be applied, as aforesaid, during curing of the hydrogel, preferably near the end of the curing process, during dehydration, or after dehydration. When the externally applied force is applied, the dimensions of the hydrogel plug will change but said stretched dimensions will be maintained when the externally applied force is removed because the elastic limit of the plug will have been exceeded. Only when the stretched plug is exposed to the natural moisture of the human body, or some other source of moisture, will it return or substantially return to the in repose size and shape it had prior to the application of the externally applied force and prior to its dehydration. Hydration is thus understood as a means for removing the stresses imparted by the externally applied force or forces. If externally applied forces are applied to a cylindrical plug, for example, to lengthen it, and if stretched beyond its elastic limit, the lengthening will reduce the diameter of the plug. Removal of the externally applied force will not further affect the shape of the plug, i.e., it will maintain its stretched size and shape. Only when hydration of the plug occurs will the diameter of the plug return to or almost to its original diameter and the length shorten to its original length. All embodiments behave in a like manner, returning to or almost to their original, unstretched or undeformed shapes and sizes only when hydrated.

These and other advantages will become apparent as this disclosure proceeds. The invention includes the features of construction, arrangement of parts, and combination of elements set forth herein, and the scope of the invention is set forth in the claims appended hereto.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
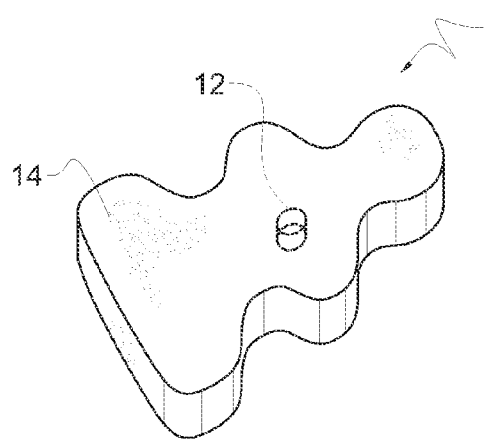
FIG. 1 is a perspective view of a first embodiment of a hydrogel plug in a position of repose.

Referring now to FIG. 1, it will there be seen that an illustrative embodiment of the invention is denoted as a whole by the reference numeral 10.

Hydrogel plug 10 includes permanent marker 12 embedded within a hydrogel material 14 having, in this first embodiment, a shape designed to inhibit migration of the plug within tissue. The FIG. 1 configuration is the "in repose" configuration of plug 10. Marker 12 is formed of metal, hard plastic, or other permanent material. It should be noted that the marker may be embedded in the center of the hydrogel or at any off center location. It may even be positioned outside the hydrogel if a record is made recording the location of the marker relative to the hydrogel.

This invention is not limited to any particular shape. Hydrogel material 14 may be formed into any shape that inhibits migration.

Permanent marker 12 could also be positioned in the interior of a balloon or other bladder and said balloon or bladder could be filled with water. Although this may not be a practical way of identifying the location of the permanent marker, it would work because water is hypoechoic and such an apparatus would therefore identify the location of a hyperechoic permanent marker.

Figure 2:
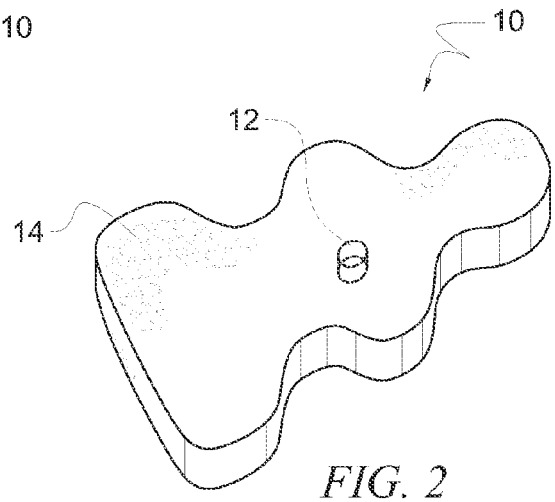
FIG. 2 is a perspective view of said hydrogel plug when stress is applied thereto in a longitudinal direction.

In FIG. 2, plug 10 is depicted when an external force is applied thereto in a longitudinal direction in excess of its elastic limit. Thus, plug 10 is therefore permanently lengthened relative to its "in repose" configuration of FIG. 1. Thus, it has a smaller diameter and a greater when stretched than when it was in repose. When the external force is removed, plug 10 substantially retains its FIG. 2 size and shape. When the manufacturing of plug 10 of FIG. 2 is completed and the finished, dehydrated plug 10 is hydrated, it returns to, or almost to, its FIG. 1 size and shape, increasing in diameter and decreasing in length.

There are different methods by which a longitudinal force may be applied to plug 10, and all of such methods are within the scope of this invention. One way is to simply pull upon the plug in a longitudinal direction. Another way is to suspend it so that gravity performs the elongation. Another way is to suspend plug 10 and employ a weight to increase the gravitational pull. In all cases, the elastic limit of the hydrogel material must be exceeded.

Figure 3:
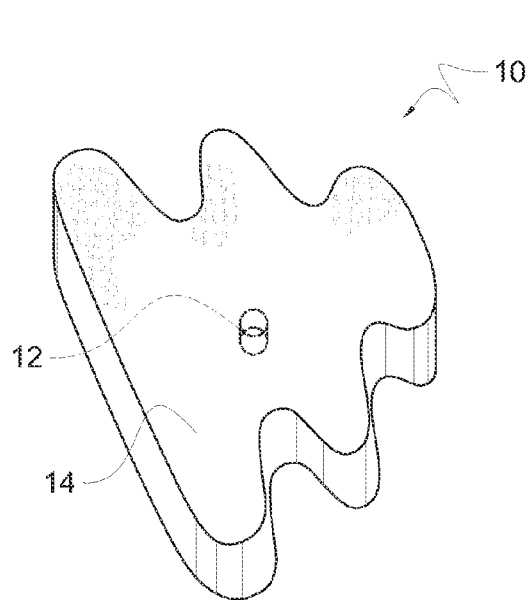
FIG. 3 is a perspective view of said hydrogel plug when stress is applied thereto in a transverse direction.

In FIG. 3, plug 10 is depicted when an external force is applied thereto in a transverse direction beyond the elastic limit of the material. Thus, plug 10 is widened relative to its "in repose" configuration of FIG. 1, but it loses some height and length. When the externally applied transverse force is removed, plug 10 substantially retains its FIG. 3 size and shape. When the manufacturing of plug 10 of FIG. 3 is completed and the finished, dehydrated plug 10 is hydrated, it contracts substantially to its FIG. 1 size and shape, thus growing shorter but higher than its stressed size and shape.

Figure 4:
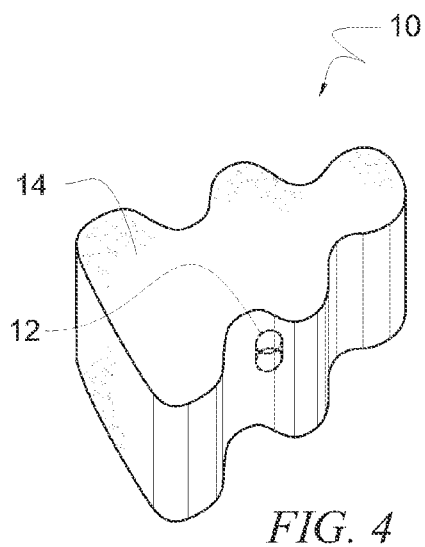
FIG. 4 is a perspective view of said hydrogel plug when stress is applied thereto in a vertical direction.

In FIG. 4, plug 10 is depicted when an external force is applied thereto in a vertical direction beyond the elastic limit of the material. Thus, the vertical dimension or depth of plug 10 is increased relative to its "in repose" configuration of FIG. 1 but its length and width are reduced. When the vertical external force is removed, plug 10 substantially retains its FIG. 4 size and shape. When the manufacturing of plug 10 of FIG. 4 is completed and the finished, dehydrated plug 10 is hydrated, it contracts to or almost to its FIG. 4 size and shape.

The terms "longitudinal," "transverse," and "vertical" as used herein are equal, respectively, to the x, y, and z coordinates of the three dimensional Cartesian coordinate system.

Figure 5:
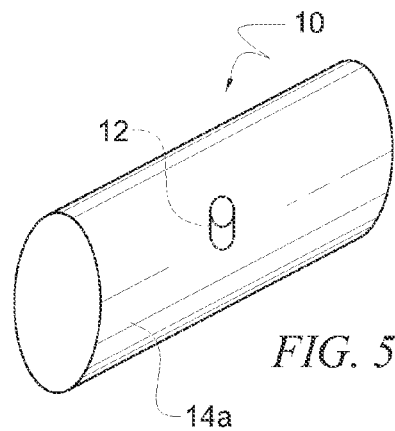
FIG. 5 is a perspective view of a cylindrical hydrogel plug when in repose.
Figure 6:
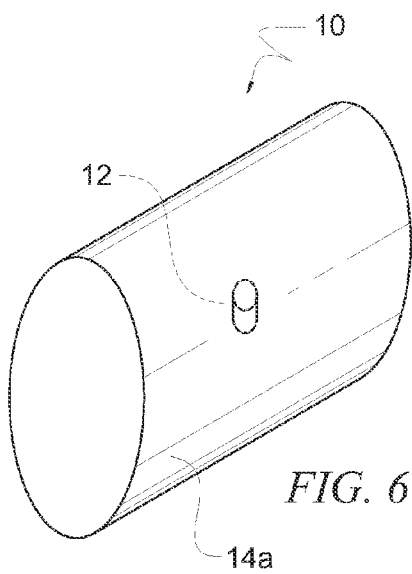
FIG. 6 is a perspective view of the cylindrical plug of FIG. 5 when said plug is expanded in a radial direction.

FIG. 5 depicts a cylindrical plug 14a in repose and FIG. 6 depicts said cylindrical plug when acted upon by externally applied radial forces, i.e., forces that radiate from the longitudinal axis of symmetry of plug 10. Such forces are most easily applied from within, so plug 10 is provided in cylinder form when radial expansion is desired. Radial forces are combinations of transverse (y) and vertical (z) forces. Plug 10, when acted upon by radial forces, is increased in diameter and shortened along its longitudinal axis. The amount of contraction is proportional to the strength of the radial forces applied. When a plurality of hydrogel plugs 14a are manufactured, a record is kept of the amount of radial expansion force applied to each batch of plugs and of the corresponding length of contraction. A ratio is calculated by dividing the radial expansion by the length of contraction, and this value, RE/LC, is applied to the batch of plugs made with such radial forces. Radial expansion is desirable when a cavity or a biopsy tract needs to be sealed in the substantial absence of longitudinal expansion. The innovative method disclosed herein enables the marker manufacturer to produce markers having known RE/LC ratios.

As in the other examples, cylindrical plug 14*a* substantially retains its FIG. 6 position when the externally applied radial forces are removed because the radial expansion exceeds the elastic limit of the plug. When the manufacturing of cylindrical plug 14*a* is completed and the finished, dehydrated plug 14*a* of FIG. 6 is hydrated, it returns to or almost to its FIG. 5 size and shape.

In the first novel method, stress is induced in the hydrogel during the curing process. This introduction of stress while the hydrogel is changing from a liquid to a solid stage creates a solid, dry marker that contracts when hydrated only in the amount and direction or directions of expansion that it experienced during the curing process. The marker will not expand to any significant degree in other way when hydrated.

In a second novel method, stress is induced during the dehydration process.

In a third novel method, stress is induced after dehydration of the polymer has been completed. The stress may also be induced by stretching or by introducing different mechanical deformations by means other than stretching. Some of these deformations are achieved by using mechanical processing equipment having various functions such as punching, folding, and the like. As aforesaid, the amount of deformation must exceed the elastic limit of the material.

Figure 7:
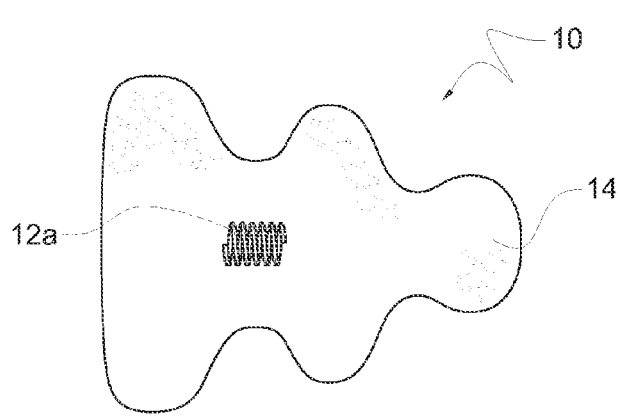
FIG. 7 is a side elevational view of a second embodiment of the permanent marker when the hydrogel plug that encapsulates it is in repose.
Figure 8:
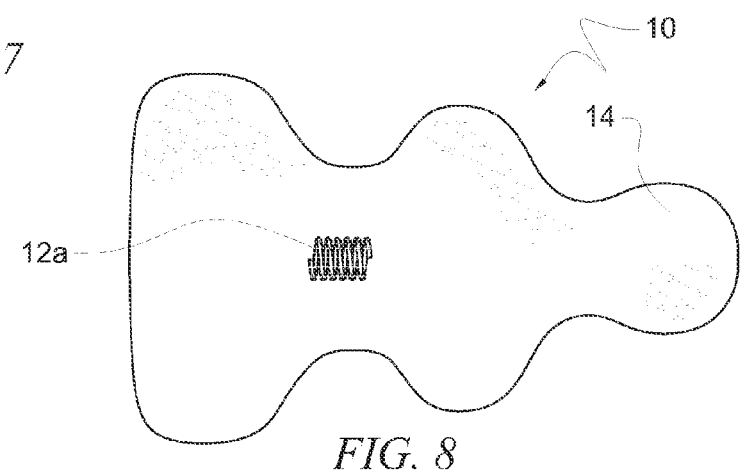
FIG. 8 is a side elevational view of said second embodiment when stress is applied thereto in a longitudinal direction.

FIG. 7 depicts an embodiment of the novel hydrogel plug where a helical coil 12*a* formed of a hyperechoic material such as metal or hard plastic is embedded within hydrogel material 14. FIG. 7 depicts the plug in repose. FIG. 8 depicts the coil when hydrogel 14 is stressed beyond its elastic limit in a longitudinal direction. Hydrogel 14 substantially returns to its pre-stressed, in repose configurations after the manufacturing process is complete and dehydrated hydrogel 14 is hydrated. The stresses are also applied during curing, during dehydration, and after dehydration, just as in the first embodiment.

The applications of this invention are not limited to permanent markers encapsulated in hydrogel for use in biopsy procedures. The same method may be used to facilitate detection of any metal, hard plastic, or other hyperechoic structures in the body such as vascular stents, surgical staples, embolization coils, radiation seed, aneuryism clips, electrode stimulation wires, prosthetic valves, stent grafts, biliary stents, drug delivery metal containers or dispensers, and the like.

In all embodiments, stress is induced during stretching or any mechanical deformation causing permanent damage. This deformation is beyond the plastic region and by definition is permanent. Accordingly, stress is maintained in the hydrogel even when the externally applied forces that cause permanent deformation are removed. Stresses are removed only during hydration and that is why the stretched, formed hydrogel wants to restore its original hydrated shape. The hydrogel returns substantially to its original hydrated shape, i.e., the shape it had right after curing and before dehydration. This is like removing residual stress by heat treating a cold worked metal piece such as springs.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A method for making a dehydrated hydrogel plug that expands in a controlled manner when hydrated, the method comprising:
   forming said hydrogel plug so that it has a predetermined geometric configuration when in a repose configuration;
   subjecting said hydrogel plug to a dehydration process;
   inducing stress into said hydrogel plug after said dehydration process by applying an external force so that said hydrogel plug is stressed beyond its elastic limit;
   controlling said stress so that said hydrogel plug, when under stress, assumes a preselected stretched geometrical configuration;
   curing said dehydrated hydrogel plug, wherein curing said dehydrated hydrogel plug comprises curing said dehydrated hydrogel plug inside a core of a coil and between loops of the coil to achieve a selected coverage of a hyperechoic marker;
   removing said externally applied force after the dehydration process so that the cured and dehydrated hydrogel plug retains said preselected geometrical configuration after said externally applied force has been removed; and
   hydrating said cured and dehydrated hydrogel plug to make said cured and dehydrated hydrogel plug substantially return to the repose configuration after the hydration process is concluded.

2. The method of claim 1, further comprising:
   inducing said stress into said hydrogel plug after said dehydration process by subjecting said hydrogel plug to an externally applied force coincident with a longitudinal axis of said hydrogel plug;
   wherein said cured and dehydrated hydrogel plug, when hydrated, contracts only in a longitudinal direction.

3. The method of claim 2, further comprising:
   inducing said stress into said hydrogel plug after said dehydration process by subjecting said dehydrated hydrogel plug to an externally applied force coincident with a transverse axis of said dehydrated hydrogel plug, said transverse axis being normal to said longitudinal axis;
   wherein said cured and dehydrated hydrogel plug, when hydrated, contracts only in a transverse direction.

4. The method of claim 3, further comprising:
   inducing said stress into said dehydrated hydrogel plug after said dehydration process by subjecting said dehydrated hydrogel plug to an externally applied force coincident with an axis normal to said longitudinal axis and normal to said transverse axis of said dehydrated hydrogel plug;
   wherein said cured and dehydrated hydrogel plug, when hydrated, contracts only in a direction normal to said longitudinal axis and normal to said transverse axis.

5. The method of claim 4, further comprising:
   inducing said stress into said dehydrated hydrogel plug after said dehydration process by subjecting said dehydrated hydrogel plug to an externally applied radial force, said radial force causing said dehydrated hydrogel plug to expand radially relative to a longitudinal axis and to contract relative to said longitudinal axis;

determining a radial expansion to longitudinal contraction ratio;

wherein said dehydrated hydrogel plug, when hydrated, contracts in a radial direction relative to said longitudinal axis and contracts along said longitudinal axis; and measuring the amount of radial expansion and the amount of longitudinal contraction and dividing the radial expansion by the longitudinal contraction to derive a radial expansion to longitudinal contraction ratio.

6. The method of claim 5, further comprising:

inducing said stress into said dehydrated hydrogel plug after said dehydration process by subjecting said dehydrated hydrogel plug to at least one externally applied deformation force.

7. The method of claim 6, wherein said at least one externally applied deformation force includes punching.

8. The method of claim 6, wherein said at least one externally applied deformation force includes folding.

\* \* \* \* \*